US008721687B2

(12) United States Patent
Butler et al.

(10) Patent No.: US 8,721,687 B2
(45) Date of Patent: May 13, 2014

(54) SPINAL IMPLANT FOR LUMBAR VERTEBRA TO SACRUM FIXATION

(75) Inventors: Michael S. Butler, Fishers, IN (US); Madeline C. Wolters, Carol Stream, IL (US); Daniel Predick, Chicago, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 0 days.

(21) Appl. No.: 13/618,708

(22) Filed: Sep. 14, 2012

(65) Prior Publication Data

US 2013/0072979 A1 Mar. 21, 2013

Related U.S. Application Data

(63) Continuation-in-part of application No. 13/247,664, filed on Sep. 28, 2011, and a continuation-in-part of application No. 13/306,744, filed on Nov. 29, 2011, now Pat. No. 8,636,771.

(60) Provisional application No. 61/417,484, filed on Nov. 29, 2010.

(51) Int. Cl.
*A61B 17/70* (2006.01)
(52) U.S. Cl.
USPC ............................................. 606/249; 606/248
(58) Field of Classification Search
USPC ............................................. 606/246–249, 90
See application file for complete search history.

(56) References Cited

U.S. PATENT DOCUMENTS

| 4,466,426 A | * | 8/1984 | Blackman | 604/187 |
| 4,636,217 A | | 1/1987 | Ogilvie et al. | |
| 5,645,599 A | | 7/1997 | Samani | |
| 5,836,948 A | | 11/1998 | Zucherman et al. | |
| 5,860,977 A | | 1/1999 | Zucherman et al. | |
| 5,876,404 A | | 3/1999 | Zucherman et al. | |
| 6,048,342 A | | 4/2000 | Zucherman et al. | |
| 6,068,630 A | | 5/2000 | Zucherman et al. | |
| 6,074,390 A | | 6/2000 | Zucherman et al. | |

(Continued)

FOREIGN PATENT DOCUMENTS

WO   WO-2006/102485   9/2006

OTHER PUBLICATIONS

"Bacfuse® Spinous Process Fusion Plate Surgical Technique", © 2011, Pioneer Surgical, 12 pages.

(Continued)

*Primary Examiner* — Michael T Schaper
*Assistant Examiner* — Tracy Kamikawa
(74) *Attorney, Agent, or Firm* — Foley & Lardner LLP

(57) ABSTRACT

A spinal implant includes a first arm comprising a first upper portion and a first lower portion extending from a first middle portion, the first upper portion, first lower portion, and first middle portion defining a first inward facing surface; a projection extending from the first middle portion; a second arm comprising a second upper portion and a second lower portion extending from a second middle portion, the second middle portion defining a bore configured to receive the projection to enable adjustment of the second arm relative to the first arm, the second upper portion, the second lower portion, and the second middle portion defining a second inward facing surface; a plurality of first spikes extending in a generally perpendicular fashion from the first and second inward facing surfaces; and at least one second spike extending in a non-perpendicular fashion from the first and second inward facing surfaces.

9 Claims, 22 Drawing Sheets

(56) References Cited

U.S. PATENT DOCUMENTS

| | | |
|---|---|---|
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,451,019 B1 | 9/2002 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,796,983 B1 | 9/2004 | Zucherman et al. |
| 7,101,375 B2 | 9/2006 | Zucherman et al. |
| 7,695,513 B2 | 4/2010 | Zucherman et al. |
| 8,231,656 B2 | 7/2012 | Lee et al. |
| 2003/0236520 A1 | 12/2003 | Lim et al. |
| 2005/0222681 A1 | 10/2005 | Richley et al. |
| 2005/0261769 A1 | 11/2005 | Moskowitz et al. |
| 2005/0278036 A1 | 12/2005 | Leonard et al. |
| 2006/0036258 A1 | 2/2006 | Zucherman et al. |
| 2006/0084988 A1 | 4/2006 | Kim |
| 2006/0089718 A1* | 4/2006 | Zucherman et al. ....... 623/17.11 |
| 2006/0241601 A1 | 10/2006 | Trautwein et al. |
| 2006/0264938 A1 | 11/2006 | Zucherman et al. |
| 2007/0142915 A1 | 6/2007 | Altarac et al. |
| 2008/0114456 A1 | 5/2008 | Dewey et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0312741 A1 | 12/2008 | Lee et al. |
| 2010/0241167 A1 | 9/2010 | Taber et al. |
| 2011/0022090 A1 | 1/2011 | Gordon et al. |
| 2011/0066186 A1* | 3/2011 | Boyer et al. .................. 606/249 |
| 2011/0144692 A1 | 6/2011 | Saladin et al. |
| 2011/0172709 A1 | 7/2011 | Lyons et al. |
| 2011/0184468 A1 | 7/2011 | Metcalf et al. |
| 2011/0224731 A1* | 9/2011 | Smisson et al. ............... 606/249 |
| 2012/0016418 A1* | 1/2012 | Chin et al. ..................... 606/249 |
| 2012/0221051 A1* | 8/2012 | Robinson ...................... 606/249 |

OTHER PUBLICATIONS

International Search Report and Written Opinion for International Application No. PCT/US2012/057324, mail date Dec. 20, 2012, 10 pages.

* cited by examiner

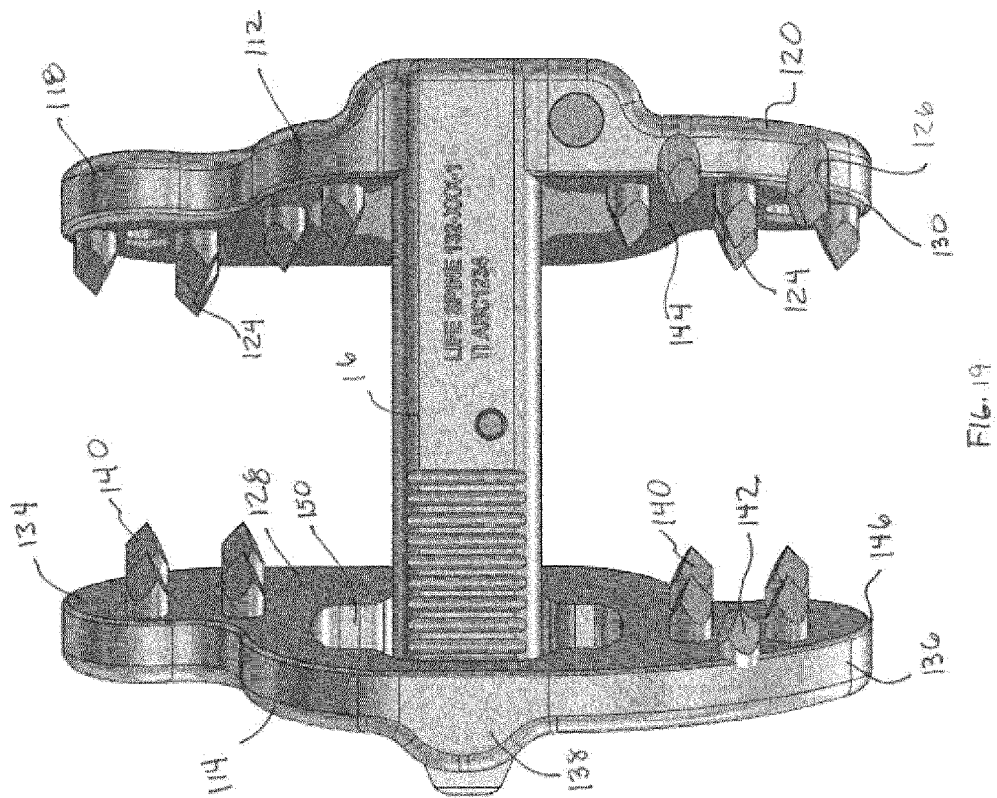

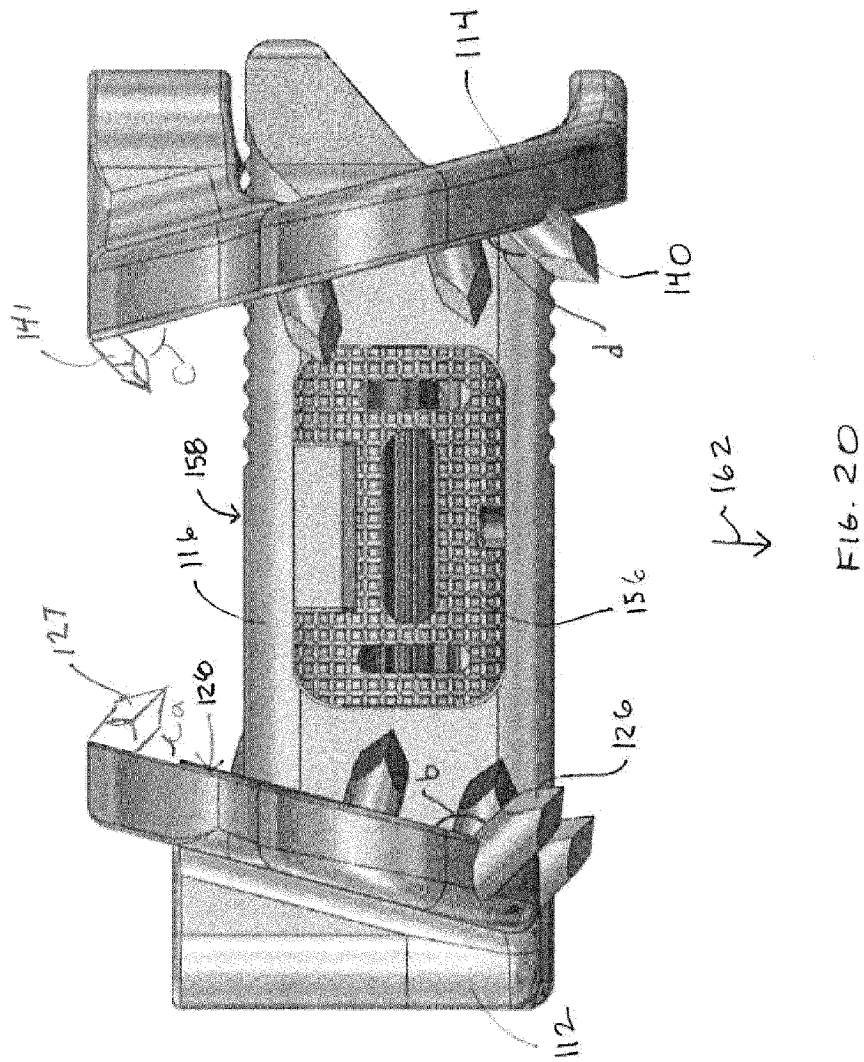

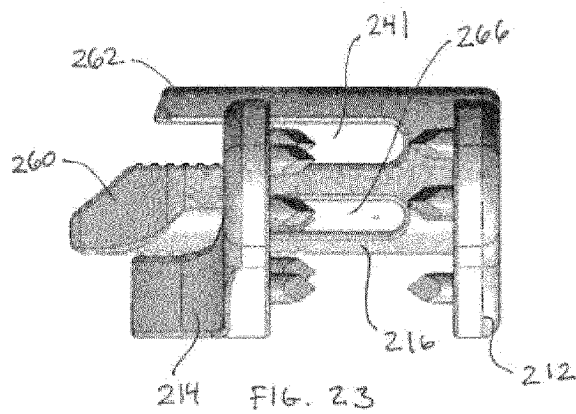
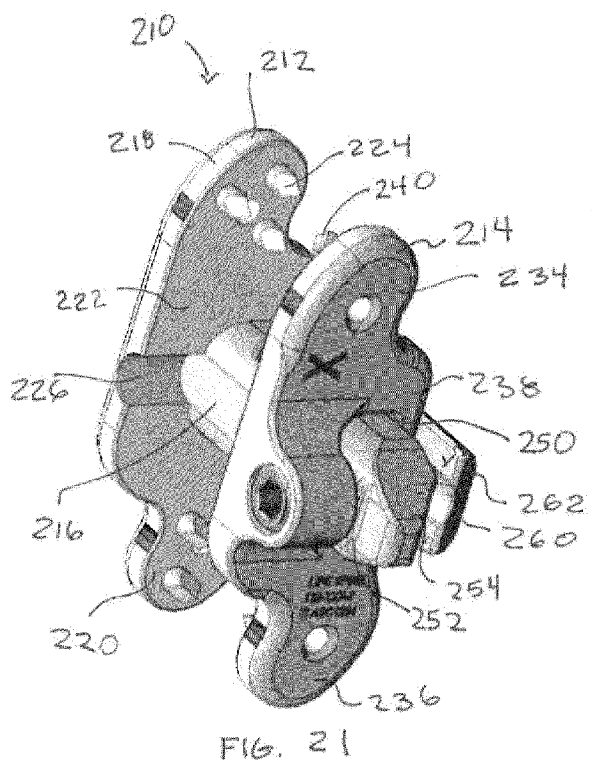
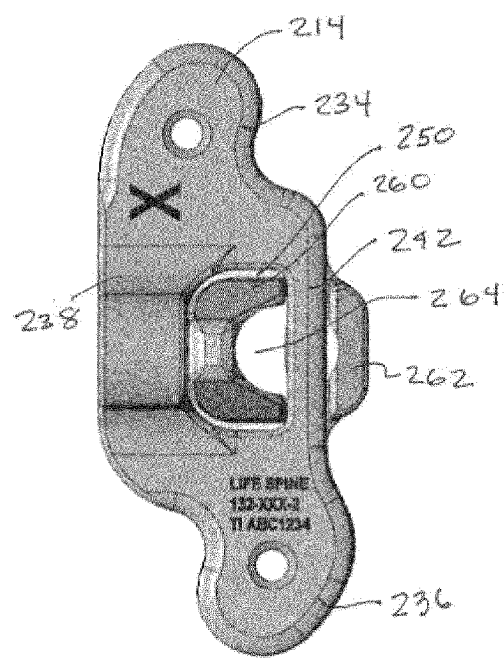

SPINAL IMPLANT FOR LUMBAR VERTEBRA TO SACRUM FIXATION

CROSS-REFERENCE TO RELATED PATENT APPLICATIONS

This application is a continuation-in-part of application Ser. No. 13/306,744, filed Nov. 29, 2011, which claims the benefit of Provisional Application No. 61/417,484, filed Nov. 29, 2010. This application is also a continuation-in-part of application Ser. No. 13/247,664, filed Sep. 28, 2011. All of these applications are incorporated by reference herein in their entireties.

BACKGROUND

The present invention relates to implants for the spine and, more particularly, to posterior spinal implants for lumbar vertebrae stabilization/fixation.

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as spinal stenosis. Spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of spinal stenosis include leg pain ("pins and needles") that can limit standing, walking, self-supporting daily activities, work, social and recreational pursuits. Lack of activity because of spinal stenosis may lead to obesity, depression and general physical deterioration.

Spinal stenosis is one of the most common reason for back surgery in people over the age of 50 in the United States. While there are various non-surgical treatments for spinal stenosis, various spinal decompression surgical procedures may be utilized to reduce or eliminate the symptoms of spinal stenosis or other spinal problems. Such procedures include a laminectomy a laminotomy, a foraminotomy or a facetectonomy.

Another surgical treatment for spinal stenosis and other spinal problems is known that is less invasive than the above surgical procedures. This other surgical treatment involves implanting a device between bony projections of adjacent vertebrae, particularly, but not necessarily, between spinous processes of the adjacent vertebrae. This achieves interspinous process decompression for alleviating spinal stenosis and other spinal problems. However, when spinal decompression, fixation or stabilization is desired between a lower lumbar vertebrae and the pelvis, prior art interspinous process decompression implants do not work.

In view of the foregoing, it is therefore desirable to provide a spinal implant for interspinous decompression of lower lumbar vertebrae relative to the pelvis. Accordingly, there exists a need for a spinal implant that provides vertebral stabilization/fixation of a lumbar vertebra relative to the pelvis.

SUMMARY

The present invention is a spinal implant for posterior vertebral stabilization and/or fixation of a lumbar vertebra relative to the pelvis. The present posterior spinal implant is particularly configured for attachment to the spinous process of a lumbar vertebra and to the sacrum of the pelvis.

The posterior spinal implant has a superior portion that is configured for attachment to the spinous process of a lumber vertebra and an inferior portion that is configured for attachment to the sacrum. Both the superior portion and the inferior portion are adjustable to allow for variations in individual bone anatomy.

In one form, the inferior portion of the present posterior spinal implant is formed by two, preferably flexible, tails each one of which is defined by a segmented band or strip that provides break points along its span for length adjustment. In this manner, each tail may be positioned and sized for fixation onto the sacrum. Additionally, each tail has a plurality of bores for receiving a bone screw to attach the tail to the sacrum. Preferably, but not necessarily, each segment of the tail has a bone screw bore in order to provide various attachment points along the length adjusted tail span.

The superior portion of this form has two titanium flanges each having a plurality of inwardly extending spikes for gripping or clamping against the sides of the spinous process. Additionally, one of the flanges is movable relative to the other flange to provide adjustability in clamping of the spinous process.

Moreover, in this form, the posterior spinal implant has a body formed as a barrel with a first transverse surface on one end of the barrel and having a first superior flange extending from the superior end of the first transverse surface and a first inferior tail as described above extending from the inferior end of the first surface for attachment to the sacrum. The first superior flange has a first plurality of spikes for engaging a first lateral side of the spinous process of a lumbar vertebra. A second transverse surface is movably carried on the barrel and has a second superior flange extending from the superior end of the second transverse surface and a second inferior tail as described above extending from the inferior end of the second transverse surface for attachment to the sacrum. The second superior flange has a second plurality of spikes for engaging a second lateral side of the spinous process of the lumbar vertebra. The second transverse surface may be fixed in position along the barrel by a fixation portion associated with the second transverse surface. In this manner, the second transverse surface and thus the second superior flange and the second inferior tail move in concert.

In another form, the posterior spinal implant has a superior or spinous process attachment portion and an inferior or sacrum attachment portion formed by a first part having a first spinous process segment of the spinous process attachment portion and a first sacrum segment of the sacrum attachment portion, and a second part having a second spinous process segment of the spinous process attachment portion and a second sacrum segment of the sacrum attachment portion. The first segments are carried on a first arm, while the second segments are carried on a second arm with the first and second arms adjustable relative to each other.

The first and second spinous process segments each have a plurality of inwardly extending spikes for gripping or clamping against the sides of the spinous process. The first and second sacrum segments each have a plurality of inwardly extending spikes for gripping or clamping against the nub of the first sacrum vertebra of the sacrum. Additionally, the first sacrum segment is angularly adjustable to provide greater variation in clamping of the sacrum. The angle of the first sacrum segment is also fixable.

Moreover, in this form, the first arm has a transverse projection that carries the second arm, the second arm being adjustable along the length of the projection. The second arm is fixable in position on the projection to provide clamping of the spinous process segments against the spinous process and of the sacrum segments against the sacrum.

In a variation of this embodiment the first and second sacrum segments each have a plurality of serrations or teeth that aid in gripping against the nub of the first sacrum vertebra.

The present posterior spinal implant is made from a biocompatible material that is preferably, but not necessarily, titanium.

BRIEF DESCRIPTION OF THE DRAWINGS

The above mentioned and other features, advantages and/or objects of this invention, and the manner of attaining them, will become apparent and the invention itself will be better understood by reference to the following description of embodiments of the invention taken in conjunction with the accompanying drawings, wherein:

FIG. 19 is a view of the anterior side of the spinal implant of FIG. 18 according to an exemplary embodiment.

FIG. 20 is a view of the inferior portion of the spinal implant of FIG. 18 according to an exemplary embodiment.

FIG. 21 is a perspective view of a spinal implant according to another exemplary embodiment.

FIG. 22 is a side view of the spinal implant of FIG. 21 according to an exemplary embodiment.

FIG. 23 is a bottom view of the spinal implant of FIG. 21 according to an exemplary embodiment.

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non-discussed features may be inherent in component geometry and/or configuration.

DETAILED DESCRIPTION OF EXAMPLE EMBODIMENTS

Figure 1:
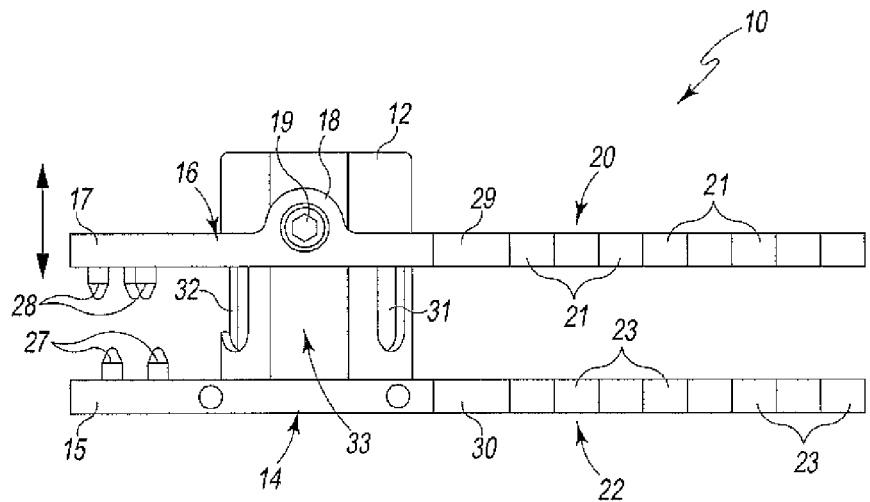
FIG. 1 is a top view of an embodiment of a posterior spinal implant for fixing a lumbar vertebra relative to the sacrum fashioned in accordance with the present principles.
Figure 2:
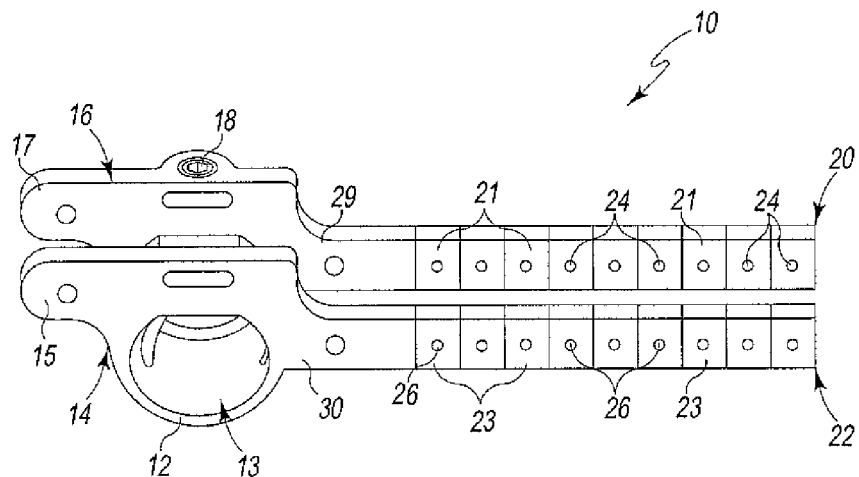
FIG. 2 is an upper side view of the posterior spinal implant of FIG. 1.
Figure 3:
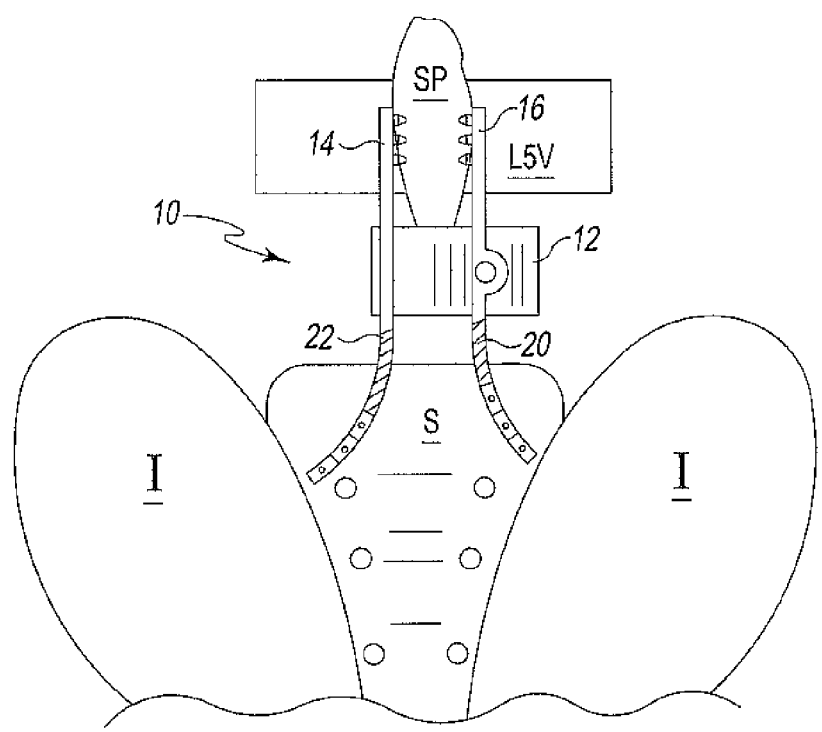
FIG. 3 is a posterior view of the posterior spinal implant of FIG. 1 attached to the spinous process of the L5 vertebra and the sacrum.
Figure 4:
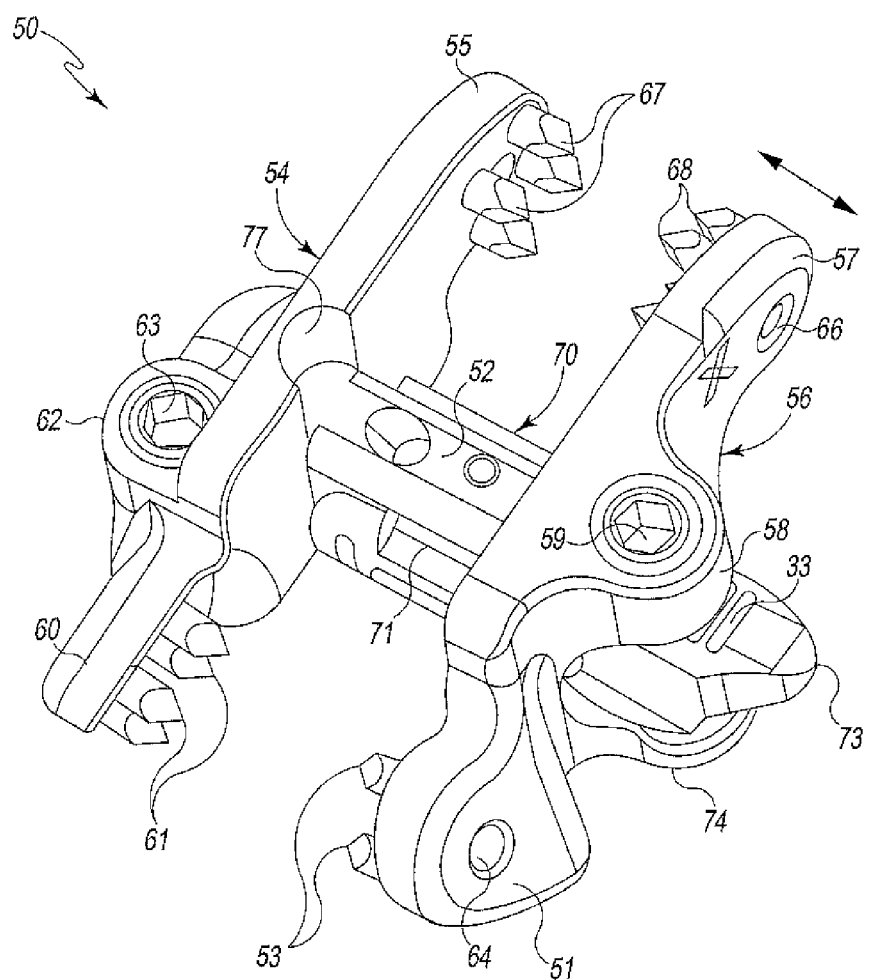
FIG. 4 is a perspective view of another embodiment of a posterior spinal implant for fixing a lumbar vertebra relative to the sacrum fashioned in accordance with the present principles.
Figure 5:
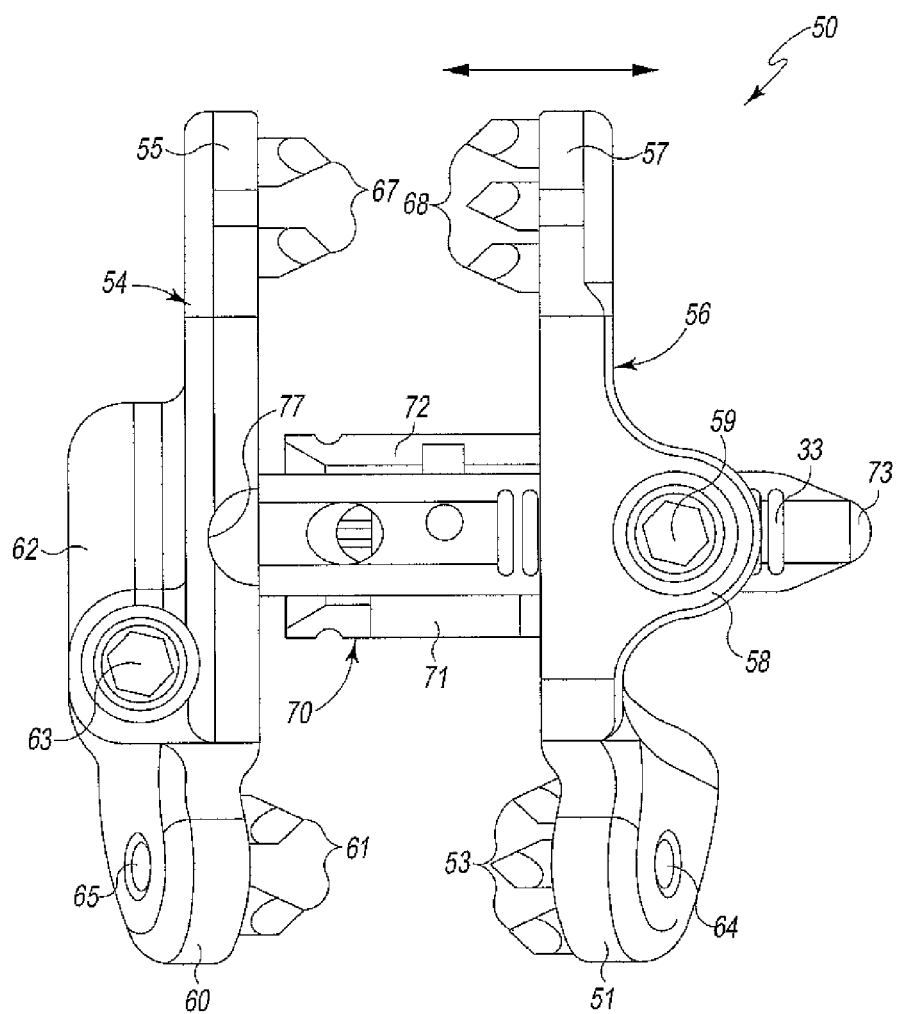
FIG. 5 is a top view of the posterior spinal implant of FIG. 4.
Figure 6:
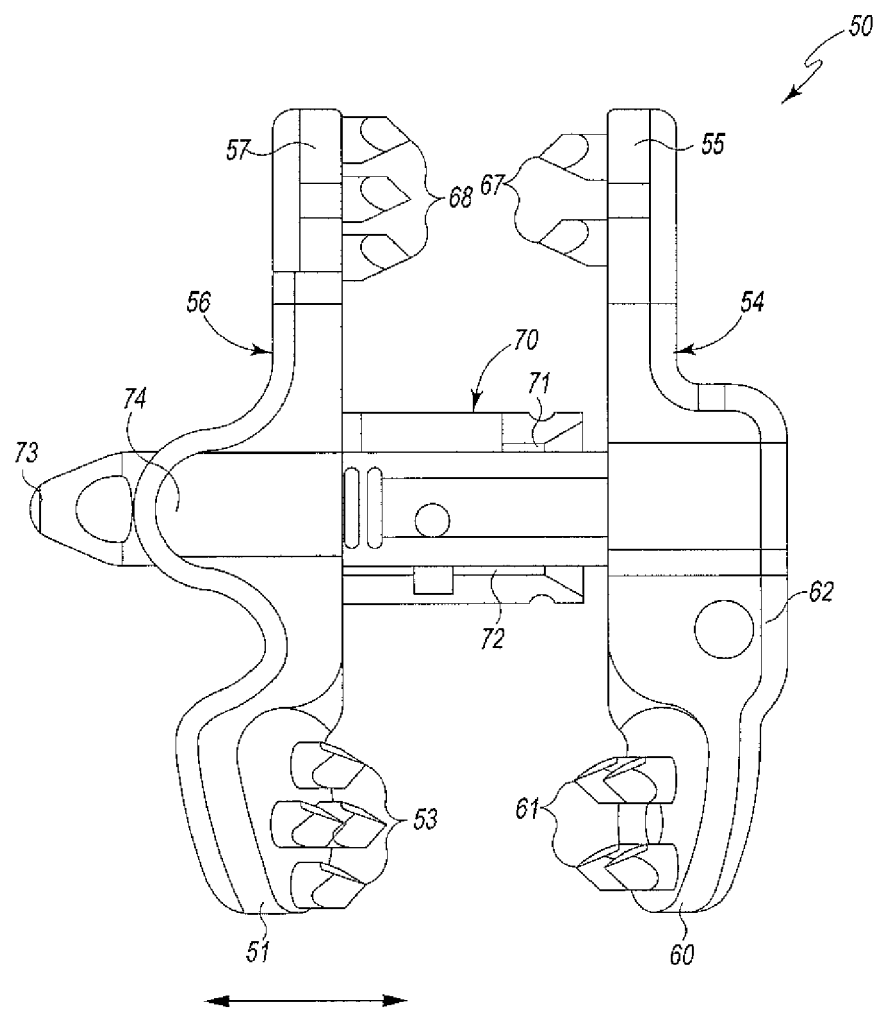
FIG. 6 is a bottom view of the posterior spinal implant of FIG. 4.

Referring to FIGS. 1 and 2, there is depicted two views of an embodiment of a spinal implant for the posterior fixation of a lumbar vertebra to the sacrum, generally designated 10 (posterior spinal implant 10), fashioned in accordance with the present principles. The posterior spinal implant 10 is designed to attach to a spinous process of a lumbar vertebrae and to the sacrum. Particularly, but not necessarily exclusively, the posterior spinal implant 10 is designed to attach to the spinous process of a lower lumbar vertebrae (e.g. the L4 or L5 vertebra) and to the sacrum. Such is seen in FIG. 3 wherein the posterior spinal implant 10 is attached to the spinous process SP of the lower lumbar L5 vertebra L5V and to the sacrum S between the left and right illiums I of the pelvis.

The posterior spinal implant 10 has a body 12 formed as a barrel or tube having a hollow tubular interior 13. A first transverse surface 14 is fixedly disposed on one transverse end of the barrel 12 and includes a first flange 15 extending from a superior end of the first transverse surface 14. As best seen in FIG. 1, the first superior flange 15 has a plurality of spikes or teeth 27 that extend inwardly from an inner surface of the first superior flange 15 and thus are designed to engage or clamp against a spinous process of the lumbar vertebra (i.e. a first transverse surface of the spinous process of the lumbar vertebra). See, for example, FIG. 3.

A first elongated flange, tail, band or strip 22 extends from a nub 30 on an inferior end of the first transverse surface 14. The first inferior tail 22 projects a length or span in the inferior direction and is defined by a plurality of segments 23. The segments 23 are scored or otherwise joined to each other to allow easy removal thereof in order to allow easy sizing of the length or span of the tail 22. Additionally, each segment 23 has a bore 26 for reception of a bone screw (not shown) for attaching the tail 22 to the sacrum S at the particular segment 23 receiving the bone screw. It should be appreciated that each segment 23 may not receive a bone screw and thus may not be attached or affixed to the sacrum. By providing a plurality of segments 23 with bores 26, the surgeon has leeway or options in attachment of the tail 22 to the sacrum.

A second transverse surface 16 is movably disposed on another transverse end of the barrel 12 and includes a second flange 17 extending from a superior end of the second transverse surface 16. As best seen in FIG. 1, the second superior flange 17 has a plurality of spikes or teeth 28 that extend inwardly from an inner surface of the second superior flange 17 and thus are designed to engage or clamp against the spinous process of the lumbar vertebra (i.e. a second transverse surface of the spinous process of the lumbar vertebra). See, for example, FIG. 3.

A second elongated flange, tail, band or strip 20 extends from a nub 29 on an inferior end of the second transverse surface 16. The second inferior tail 20 projects a length or span in the inferior direction and is defined by a plurality of segments 21. The segments 21 are scored or otherwise joined to each other to allow easy removal thereof in order to allow easy sizing of the length or span of the tail 20. Additionally, each segment 21 has a bore 24 for reception of a bone screw (not shown) for attaching the tail 20 to the sacrum S at the particular segment 21 receiving the bone screw. It should be appreciated that each segment 21 may not receive a bone screw and thus may not be attached or affixed to the sacrum. By providing a plurality of segments 21 with bores 24, the surgeon has leeway or options in attachment of the tail 20 to the sacrum.

As indicated above, the first transverse surface 14 is fixed to the barrel 12 while the second transverse surface 16 is movable along the barrel 12 and thus away from and towards the first transverse surface 14 as indicated by the double-headed arrow in FIG. 1. The first superior flange 15 and the first inferior tail 22 are thus fixed relative to the barrel 12, while the second superior flange 17 and the second inferior tail 20 are movable along the barrel 12 and thus away from and towards the first superior flange 15 and the first inferior tail 22. In this manner, the first and second superior flanges 15, 17 and their respective spikes 27, 28 provide clamping against a spinous process of a vertebra.

The barrel 12 includes a first groove 31 on an outer surface of a side thereof and a second channel 32 on the outer surface of another side thereof. The second transverse surface 17 includes projections that fit into the channels 31, 32 in order to retain and prevent rotation of the second transverse surface 17 on the barrel 12. Additionally, the barrel 12 includes a grooved flat 33 that provides stepped demarcations. A boss 18 is provided on the second transverse surface 16 that is positioned over the flat 33 and which holds a set screw 19. In this manner, the second transverse surface 16 may be fixed relative to the barrel 12 after the second transverse surface 16 is properly positioned.

The first and second inferior tails 22, 20 may be bent as necessary in order to properly position them relative to the sacrum for attachment thereof. This allows the wider flat portion of each tail to lie against the sacrum. Thereafter, one or more segments of each tail is affixed or attached to the sacrum via bone screws through their respective segment bore (see FIG. 3).

Referring to FIGS. 4-7, there is depicted various views of another embodiment of a spinal implant for the posterior fixation of a lumbar vertebra to the sacrum, generally designated 50 (posterior spinal implant 50), fashioned in accordance with the present principles. The posterior spinal implant 50 is designed to attach to a spinous process of a lumbar vertebrae and to the sacrum. Particularly, but not necessarily exclusively, the posterior spinal implant 50 is designed to attach to the spinous process of a lower lumbar vertebrae (e.g. the L5 vertebra) and to the sacrum. Such is seen in FIGS. 8-11 wherein the posterior spinal implant 50 is attached to the spinous process SP of the lower lumbar L5 vertebra L5V and to the sacrum S between the left and right illiums I of the pelvis.

The posterior spinal implant 50 has a first member or arm 54 and a second member or arm 56 that is adjustably situated on the first member 54. The first arm 54 has a projection 70 extending transverse to the arm 54. The projection 70 may be adjustable in the anterior/posterior direction as retained in channel 77 of the arm 54. The second arm 56 is movably carried on the projection 70 so that the second arm 56 is adjustable along its length (as indicated by the double-headed arrow). The adjustability of the second arm 56 along the length of the projection 70 and adjusts the distance between the first and second arms 54, 56. This provides a clamp or clamping feature as between the first and second arms 54, 56 to clamp onto or grip against the spinous process on one end thereof (a spinous process attachment portion) and the sacrum at the other end thereof (a sacrum attachment portion).

The first arm 54 has a first superior flange or spinous process segment 55 of the spinous process attachment portion having a plurality of spikes or teeth 67 that extend inwardly from an inner surface of the first spinous process segment 55 which are designed/configured to engage or clamp against a spinous process of the lumbar vertebra (i.e. a first transverse surface of the spinous process of the lumbar vertebra) such as depicted in FIGS. 8-11. The first spinous process segment 55 also may have a bore 69 for receipt of a bone screw (not shown). The optional addition of a bone screw would aid in retention of the first spinous process segment 55 onto the spinous process. The second arm 56 has a second superior flange or spinous process segment 57 of the spinous process attachment portion having a plurality of spikes or teeth 68 that extend inwardly from an inner surface of the second spinous process segment 57 which are designed/configured to engage or clamp against the spinous process of the lumbar vertebra (i.e. a second transverse surface of the spinous process of the lumbar vertebra) as depicted in FIGS. 8-11. The second spinous process segment 57 also may have a bore 66 for receipt of a bone screw (not shown). The optional addition of a bone screw would aid in retention of the second spinous process segment 57 onto the spinous process.

Figure 7:
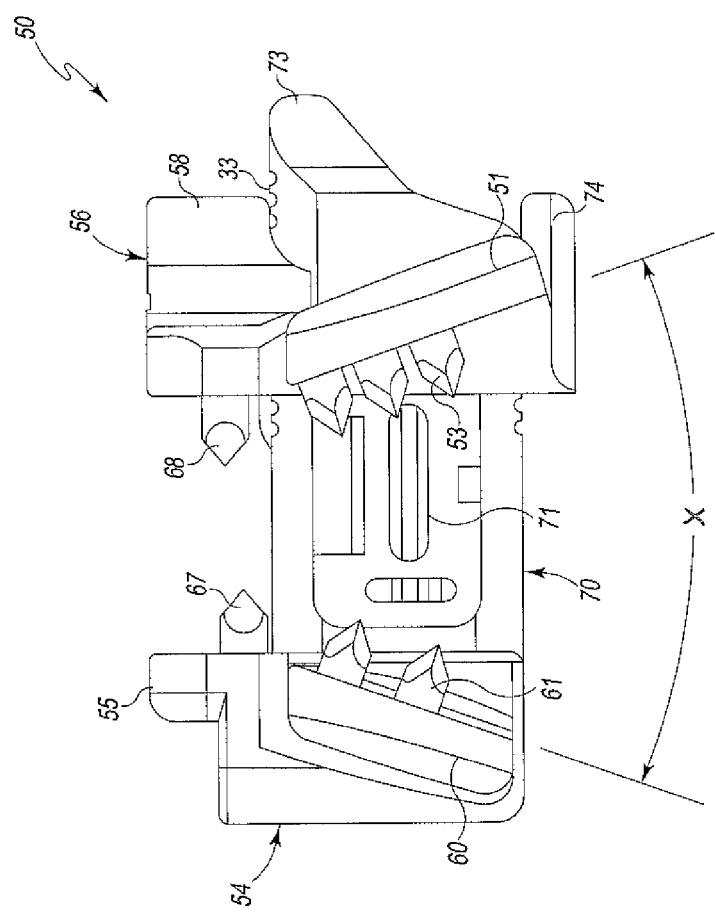
FIG. 7 is an inferior view of the posterior spinal implant of FIG. 4 particularly illustrating angling of the sacrum attachment portion thereof.
Figure 8:
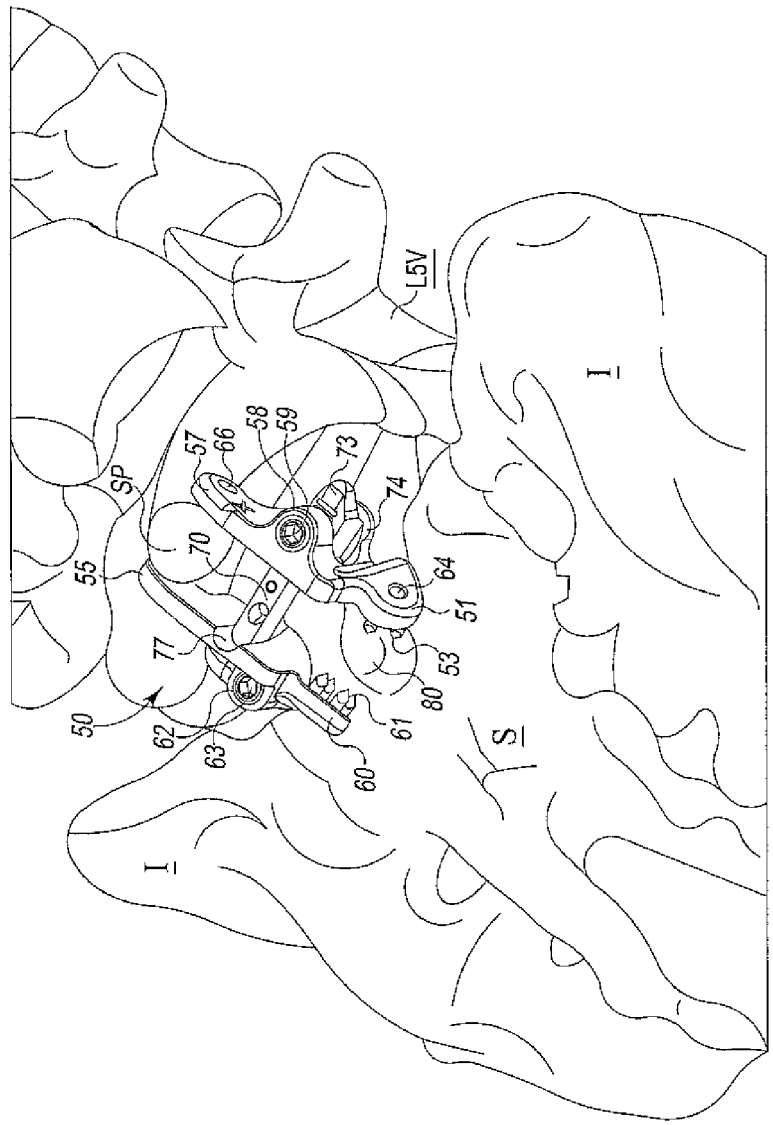
FIG. 8 is an upper, generally lateral side view of the posterior spinal implant of FIG. 4 attached to the spinous process of the L5 vertebra and the sacrum.

The first arm 54 has a first inferior flange or sacrum segment 60 of the sacrum attachment portion having a plurality of spikes or teeth 61 that extend generally inwardly and downwardly from an inner surface of the first sacrum segment 60 which are designed/configured to engage or clamp against a sacrum (i.e. a transverse side/surface of the protuberance 80 of the sacrum) such as depicted in FIGS. 8-11. The second arm 56 has a second inferior flange or sacrum segment 51 of the sacrum attachment portion having a plurality of spikes or teeth 53 that extend generally inwardly and downwardly from an inner surface of the second sacrum segment 51 which are designed/configured to engage or clamp against the sacrum (i.e. another transverse side/surface of the protuberance 80 of the sacrum) such as depicted in FIGS. 8-11. As best shown in FIG. 7, the first and second sacrum segments 60, 51 are angled downwardly providing an angle x between them, off of perpendicular. In one embodiment, x is approximately 40 degrees. In other embodiments, angle x may be more or less than 40 degrees.

The first sacrum segment 60 also may have a bore 65 for receipt of a bone screw (not shown). The optional addition of a bone screw would aid in retention of the first sacrum segment 55 onto the sacrum. Likewise, the second sacrum segment 51 also may have a bore 64 for receipt of a bone screw (not shown). The optional addition of a bone screw would aid in retention of the second sacrum segment 51 onto the sacrum.

Figure 9:
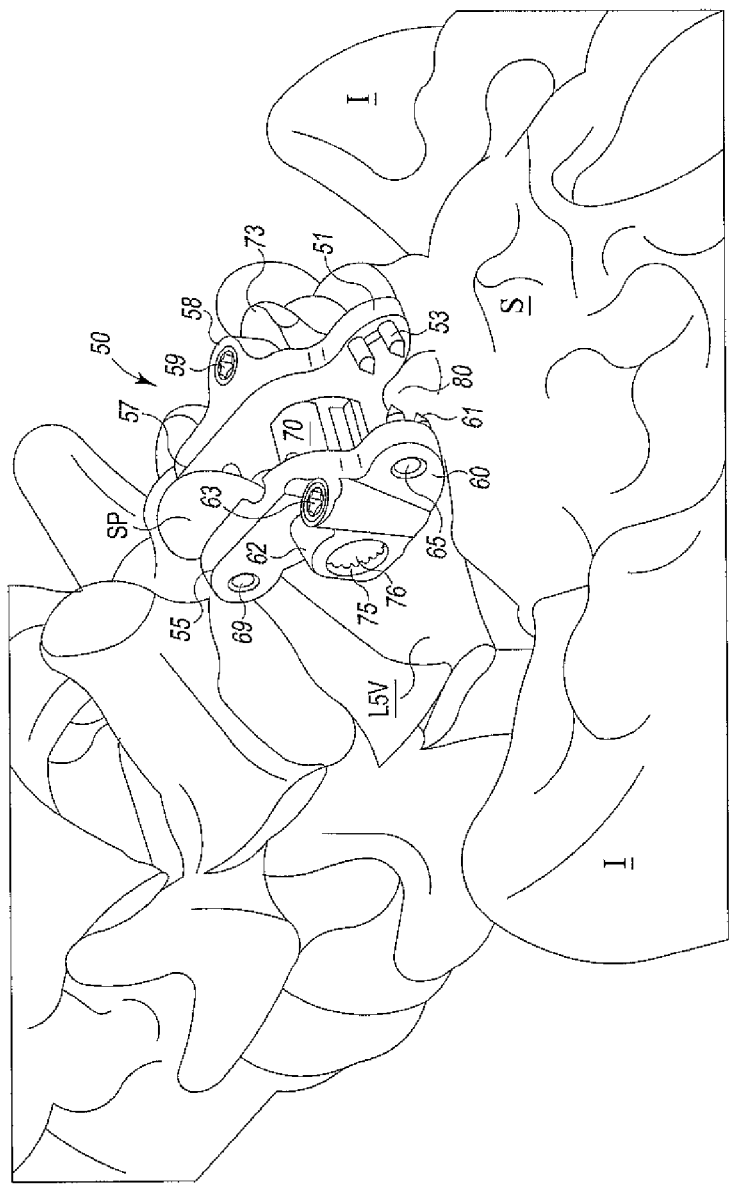
FIG. 9 is an upper, generally medial side view of the posterior spinal implant of FIG. 4 attached to the spinous process of the L5 vertebra and the sacrum.
Figure 10:
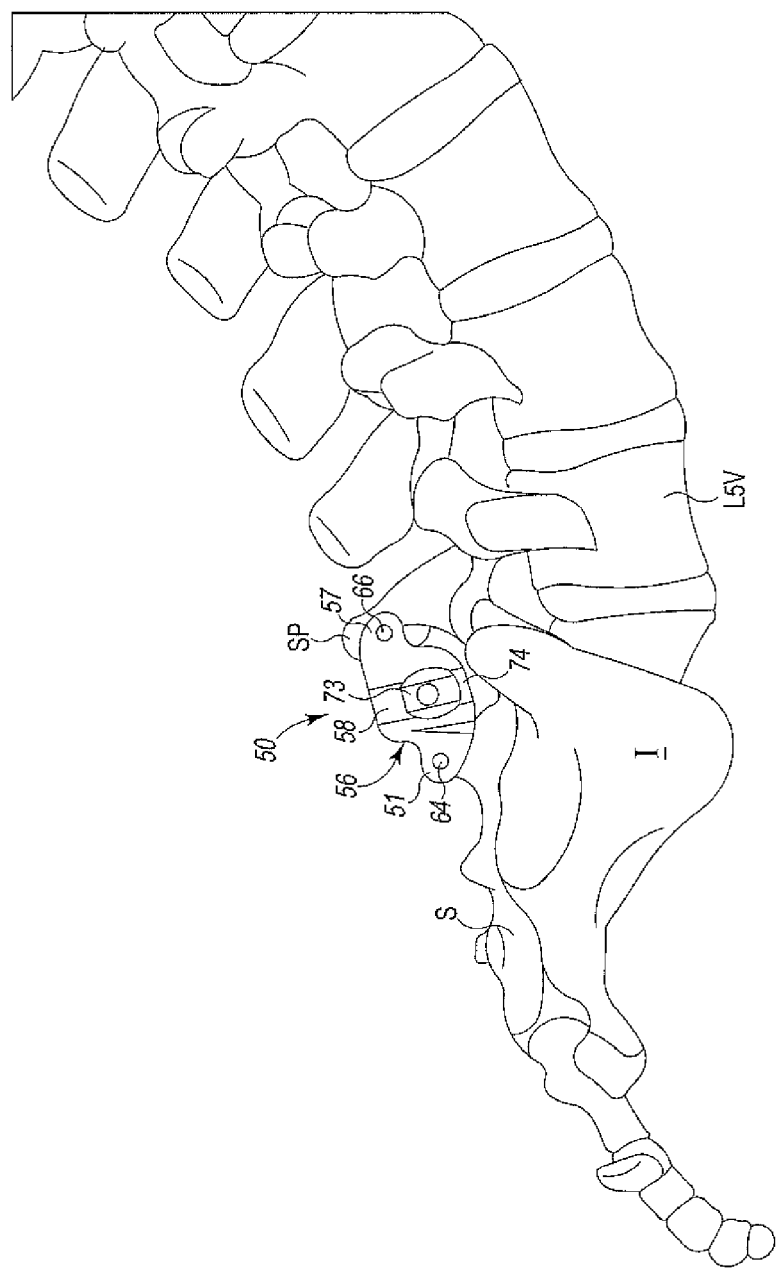
FIG. 10 is a lateral side view of the posterior spinal implant of FIG. 4 attached to the spinous process of the L5 vertebra and the sacrum.
Figure 11:
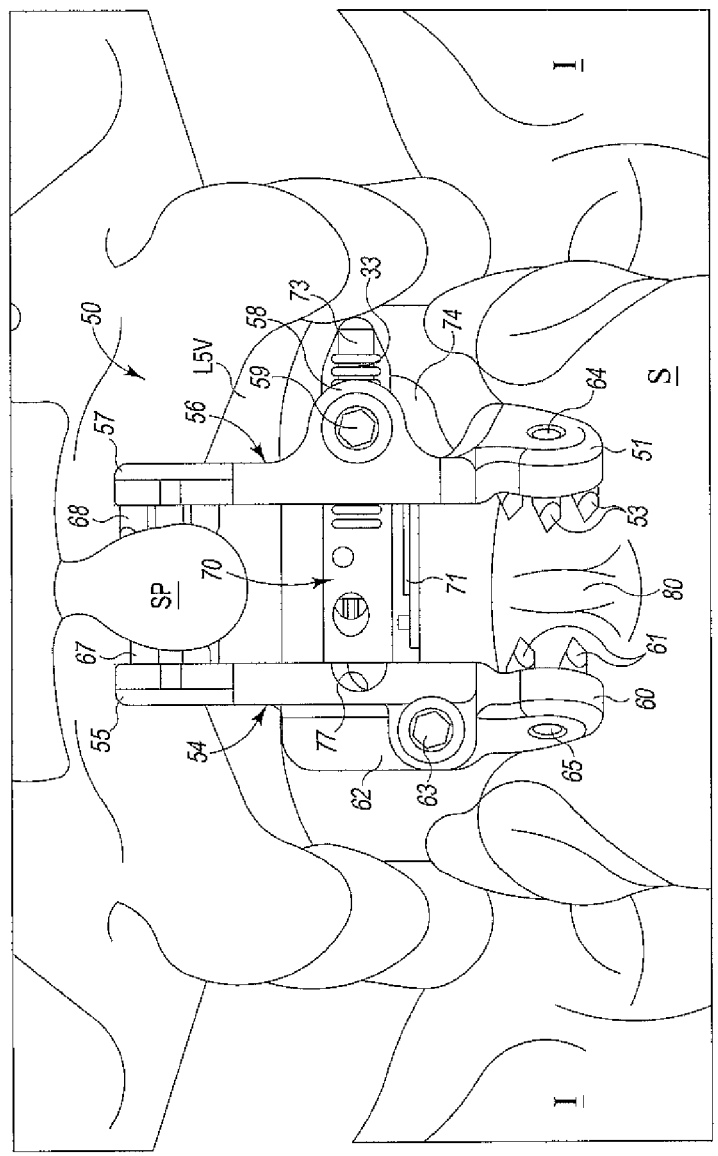
FIG. 11 is a posterior view of the posterior spinal implant of FIG. 4 attached to the spinous process of the L5 vertebra and the sacrum.

The first arm 54 is fixed to the projection 70 in a transverse direction, but able to rotation relative thereto. As best seen in FIG. 9, an end 76 of the projection 70 is situated in a bore 75 of a boss 62 of the first arm 54. This allows the first arm 54 to rotate about the projection 70. The end 76 has peripheral teeth that allow the first arm 54 to be fixed in rotational position relative to the projection 70 via a set screw 63 situated in the boss 62.

As indicated above, the second arm 56 is movable along the projection 70 and thus relative to the first arm 54. This allows the first and second arms 54, 56 and thus the first and second spinous process segments 55, 57 of the spinous process attachment portion and the first and second sacrum segments 60, 51 of the sacrum attachment portion to clamp against the spinous process SP of the lumbar vertebra L5V and the sacrum protuberance 80 of the sacrum S, and to adapt to variations in individual anatomy. The second arm 56 has a bore therein with a transverse extending ledge 74 through which the projection 70 extends. The projection has first and second channels 71, 72 that allow the second arm 56 to be guided along the projection 70. The top surface 52 of the projection 70 has a plurality of grooves or notches 33 that extend to an end 73 of the projection. The second arm 56 has a boss 58 which holds a set screw 59. The set screw 59 in conjunction with the grooves 33 allows the second arm 56 to be fixed in position relative to the projection 70.

Figure 12:
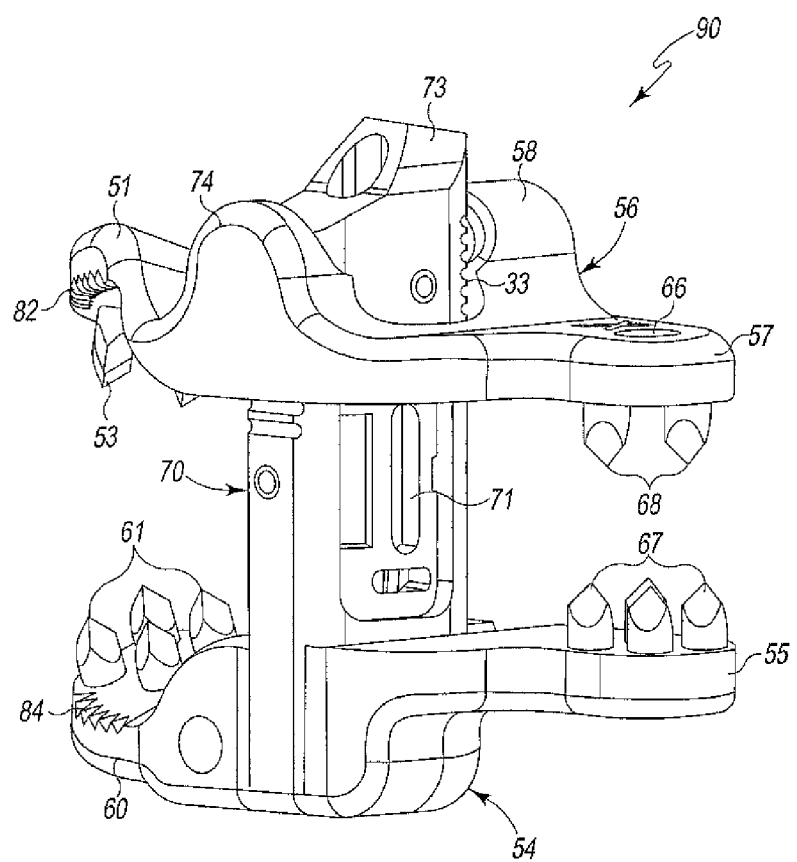
FIG. 12 is a perspective view of another embodiment of a posterior spinal implant for fixing a lumbar vertebra relative to the sacrum fashioned in accordance with the present principles.
Figure 13:
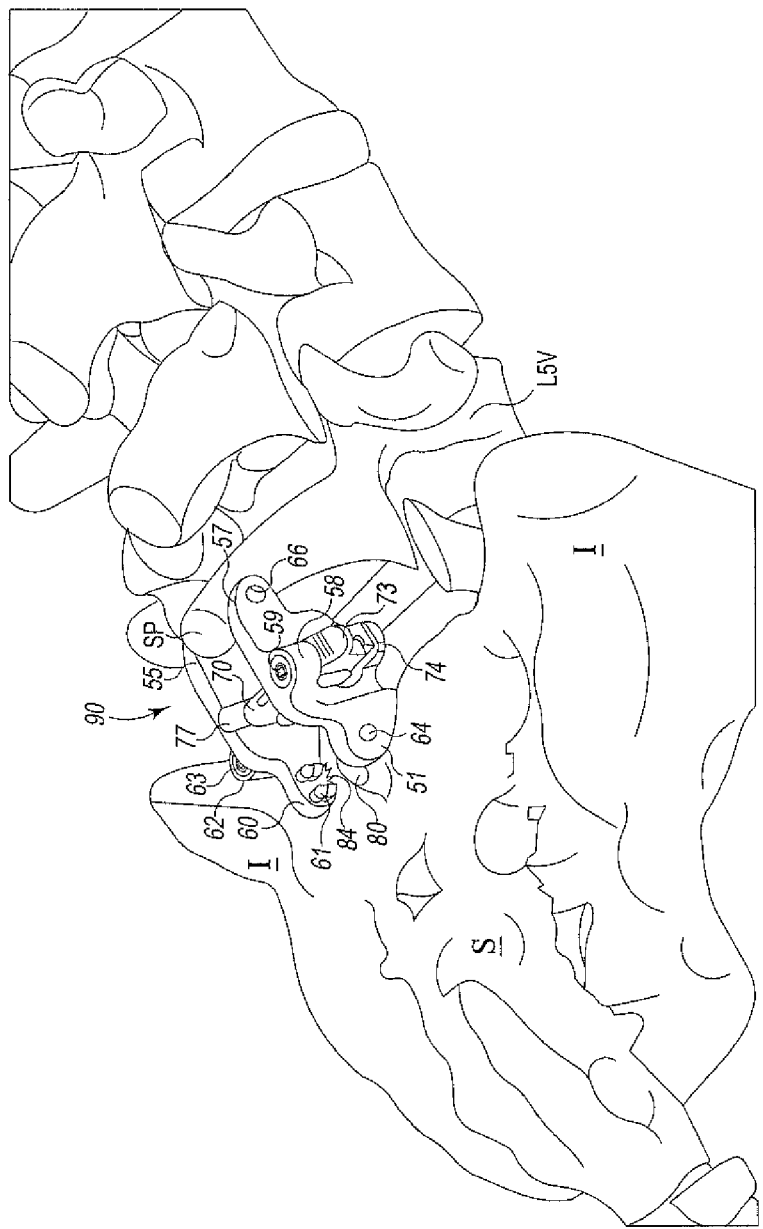
FIG. 13 is an upper, generally lateral side view of the posterior spinal implant of FIG. 12 attached to the spinous process of the L5 vertebra and the sacrum.
Figure 14:
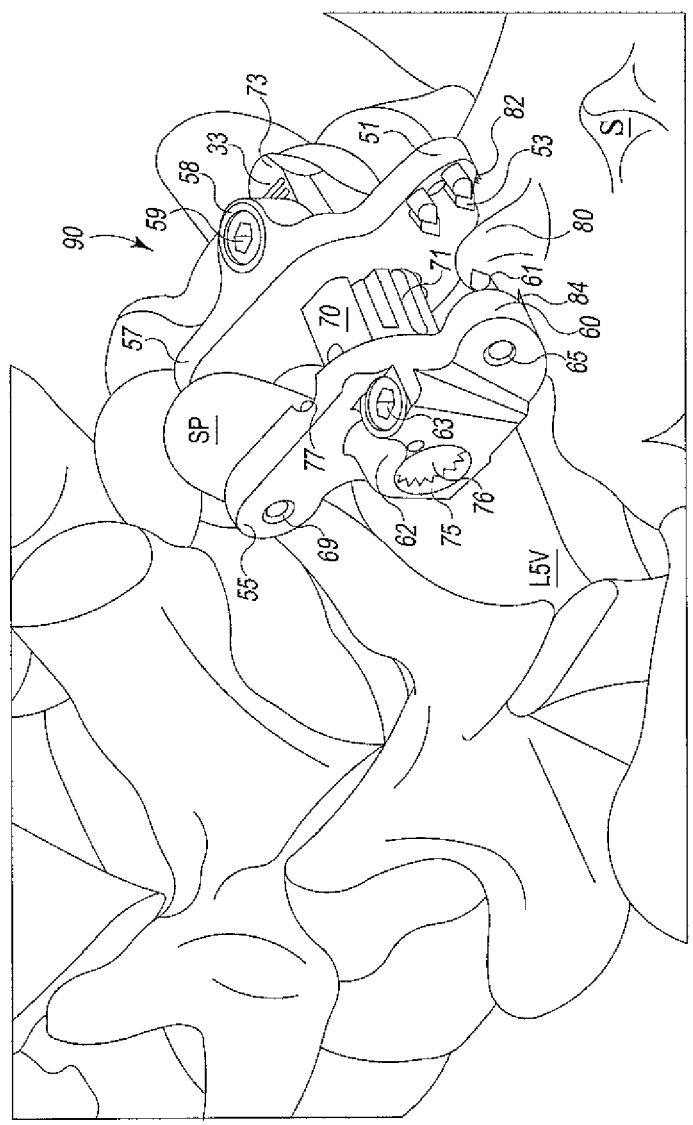
FIG. 14 is an upper, generally medial side view of the posterior spinal implant of FIG. 12 attached to the spinous process of the L5 vertebra and the sacrum.
Figure 15:
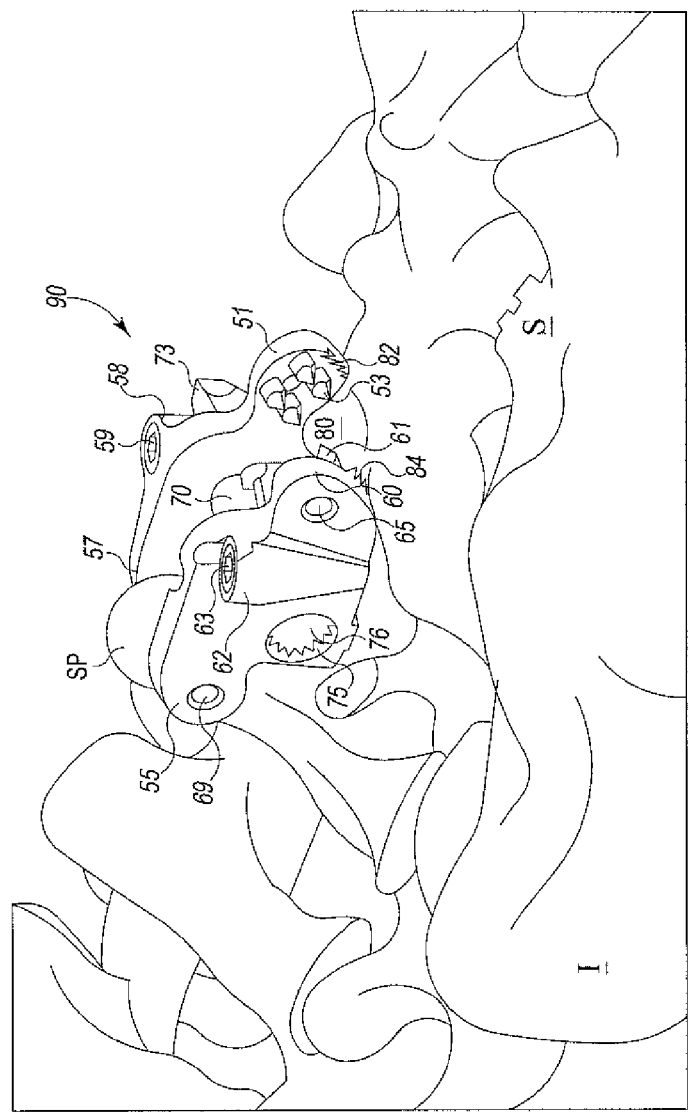
FIG. 15 a generally medial side view of the posterior spinal implant of FIG. 12 attached to the spinous process of the L5 vertebra and the sacrum.
Figure 16:
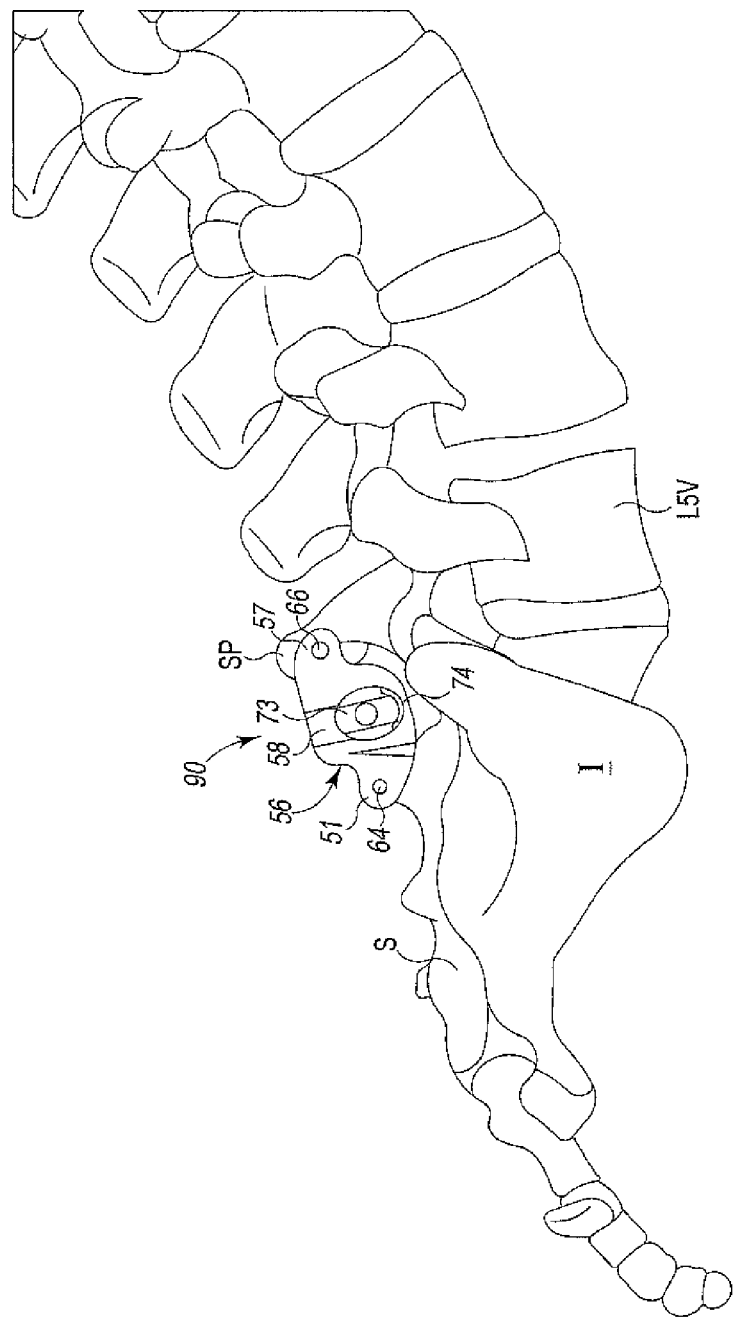
FIG. 16 is a lateral side view of the posterior spinal implant of FIG. 12 attached to the spinous process of the L5 vertebra and the sacrum.
Figure 17:
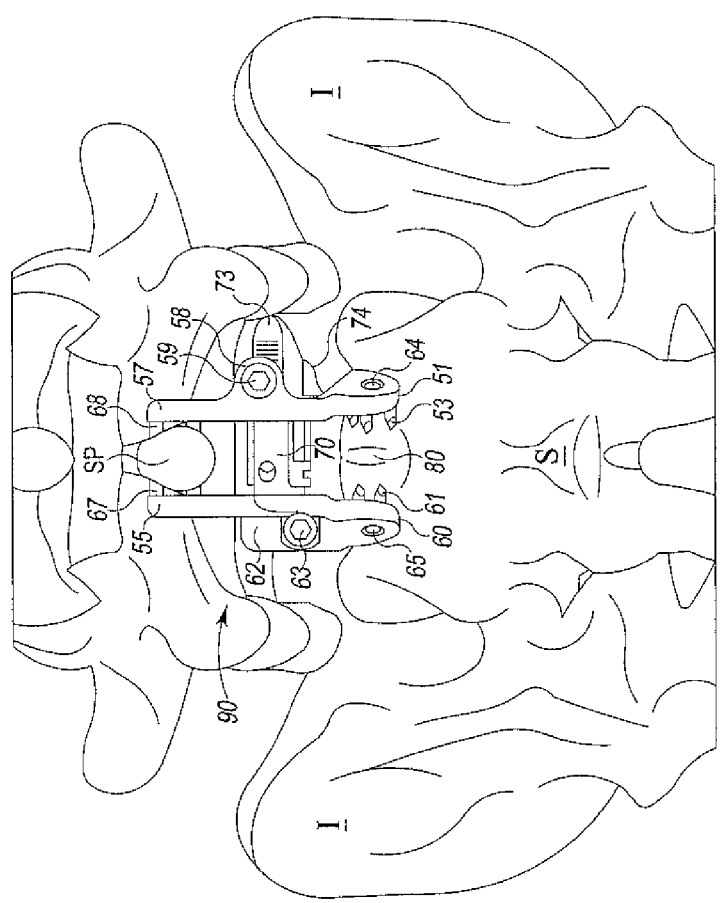
FIG. 17 is an inferior/posterior view of the posterior spinal implant of FIG. 12 attached to the spinous process of the L5 vertebra and the sacrum.

FIG. 12 depicts a spinal implant 90 having a minor variation to the spinal implant 50. Particularly, the spinal implant 90 includes a first set of teeth ("fish teeth") or the like 84 on a lower edge of the first sacrum segment 60 of the first arm 54. Likewise, the spinal implant 90 includes a second set of teeth ("fish teeth") or the like 82 on a lower edge of the second sacrum segment 51 of the second arm 56. The teeth 82, 84 provide extra gripping or clamping against the protuberance 80 of the sacrum. The spinal implant 90 is depicted in various views in FIGS. 13-17 affixed to the spinous process SP of the lumbar vertebra L5V and the protuberance 80 of the sacrum S.

Referring now to FIGS. 18-25, various additional spinal implants are shown according to alternative embodiments. It should be noted that the various features shown with respect to the spinal implants of FIGS. 18-25 may be combined with each other and/or any of the features of spinal implants disclosed elsewhere herein, and all such combinations of features are understood to be within the scope of the present disclosure.

Figure 18:
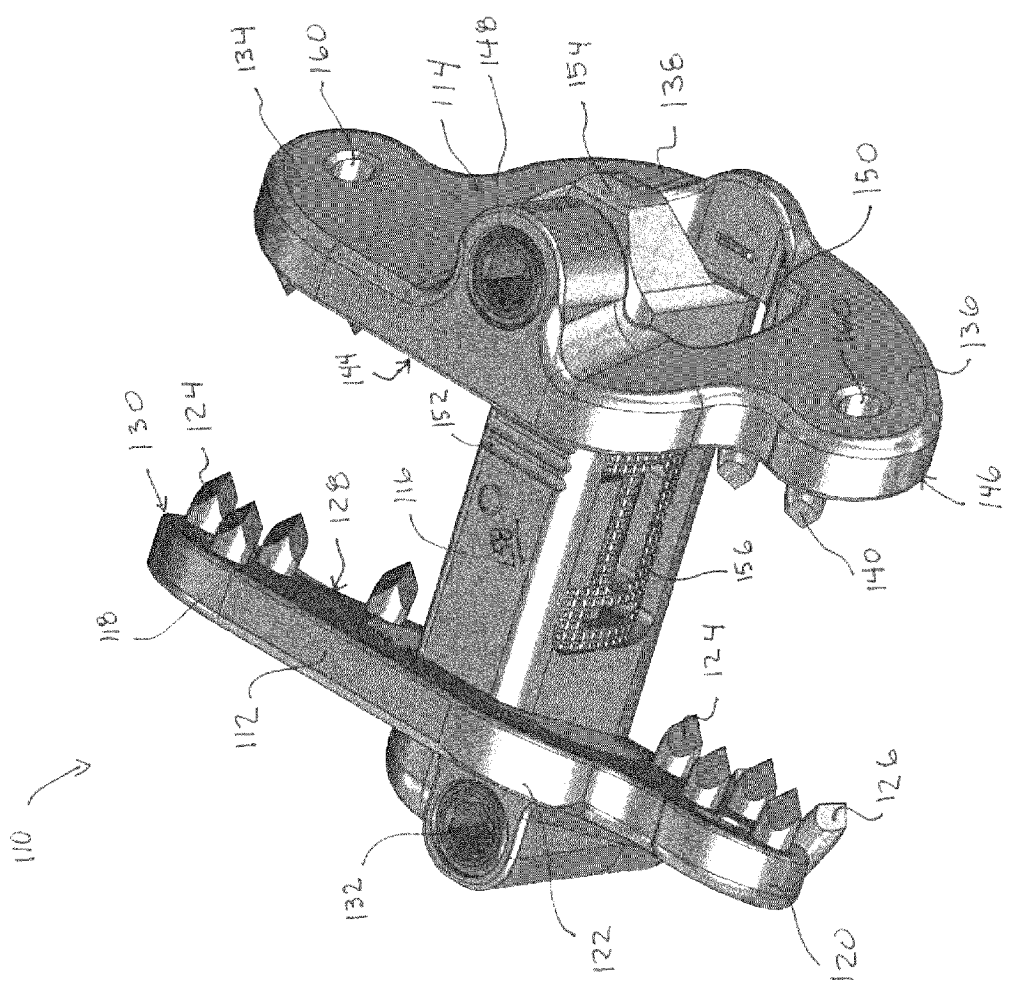
FIG. 18 is a perspective view of a spinal implant according to another exemplary embodiment.

Referring to FIGS. 18-20, a spinal implant 110 is shown according to an exemplary embodiment. Implant 110 may be secured to a spinous process of a lumbar vertebrae (e.g., the L5 vertebrae) and to the sacrum (e.g., between the left and right illiums of the pelvis). According to various alternative embodiments, implant 110 may be utilized in other portions of the spinal column.

In one embodiment, implant 110 includes a first arm 112 (e.g., a first plate, member, etc.), a second arm 114 (e.g., a second plate, member, etc.), and a projection 116 (e.g., an elongated member, etc.). Projection 116 is coupled to first arm 112, and second arm 114 is adjustably coupled to projection 116 to enable adjustment of second arm 114 relative to first arm 112 to accommodate variations in vertebral structures. The adjustability of second arm 114 also enables first and second arms 112, 114 to act as a clamp to provide a clamping force on, for example, a spinous process of a lumbar vertebrae and/or a portion of the sacrum.

According to an exemplary embodiment, first arm 112 includes an upper portion 118 (e.g., an upper flange, clamp member, wing, etc.) and a lower portion 120 (e.g., a lower flange, clamp member, wing, etc.) that both extend from a middle portion 122. Upper portion 118, lower portion 120, and middle portion 122 define an inward facing surface 128. According to an exemplary embodiment, inward facing surface 128 is a generally planar surface having a peripheral edge 130. A plurality of spikes 124 (e.g., projections, teeth, gripping members, pointed members, etc.) extend from surface 128. In one embodiment, spikes 124 extend from surface 128 in a generally perpendicular fashion, while in other embodiments, some or all of spikes 124 may extend from surface 128 in a non-perpendicular fashion (e.g., to define an acute angle a between spike 127 and surface 128 and/or to define an obtuse angle between spike 126 and surface 128). As shown in FIGS. 18-20, spikes 124 may be provided on both upper portion 118 and lower portion 120 of first arm 112.

First arm 112 further includes one or more angled spikes 126 (e.g., projections, teeth, gripping members, pointed members, etc.). As shown in FIGS. 18-20, angled spikes 126 extend from lower portion 120 in an at least partially anterior fashion. Angled spikes 126 may provide additional gripping of first arm 112 to, for example, the sacrum. According to an exemplary embodiment, spikes 124 and/or spikes 126 may have a generally cylindrical body portion and a pointed tip portion extending outward from the cylindrical portion. In other embodiments, spikes 124, 126 may take other shapes and/or sizes.

Similar to first arm 112, second arm 114 includes an upper portion 134 (e.g., an upper flange, clamp member, wing, etc.) and a lower portion 136 (e.g., a lower flange, clamp member, wing, etc.) that both extend from a middle portion 138. Upper portion 134, lower portion 136, and middle portion 138 define an inward facing surface 144. According to an exemplary embodiment, inward facing surface 144 is a generally planar surface having a peripheral edge 146. A plurality of spikes 140 (e.g., projections, teeth, gripping members, pointed members, etc.) extend from surface 144. In one embodiment, spikes 140 extend from surface 144 in a generally perpendicular fashion, while in other embodiments, some or all of spikes 140 may extend from surface 144 in a non-perpendicular fashion (e.g., to define an acute angle c between spike 141 and surface 144 and/or to define an obtuse angle d between spike 140 and surface 144). As shown in FIGS. 18-20, spikes 140 may be provided on both upper portion 134 and lower portion 136 of second arm 114.

Second arm 114 further includes one or more angled spikes 142 (e.g., projections, teeth, gripping members, pointed members, etc.). As shown in FIGS. 18-20, angled spikes 142 extend from lower portion 136 in an at least partially anterior fashion. Spikes 142 may be further configured to point at least partially downward once implanted. Angled spikes 142 may provide additional gripping of second arm 114 to, for example, the sacrum. According to an exemplary embodiment, spikes 140 and/or spikes 142 may have a generally cylindrical body portion and a pointed tip portion extending outward from the cylindrical portion. In other embodiments, spikes 140, 142 may take other shapes and/or sizes.

According to an exemplary embodiment, angled spikes 126, 142 extend from the peripheral edges 130, 146, of surfaces 128, 144 at an obtuse angle. According to an exemplary embodiment, the angle is approximately 120 degrees relative to surfaces 128, 144. In other embodiments, the angle may be between approximately 110 and 130 degrees. In further embodiments, the angle may be any angle up to 180 degrees. In other embodiments, spikes 126, 142 extend at different angles relative to surfaces 128, 144 to provide different engagement angles and results. In yet further embodiments, spikes 126, 142 extend from lower portions 120, 136 of first and second arms 112, 114.

Figure 25:
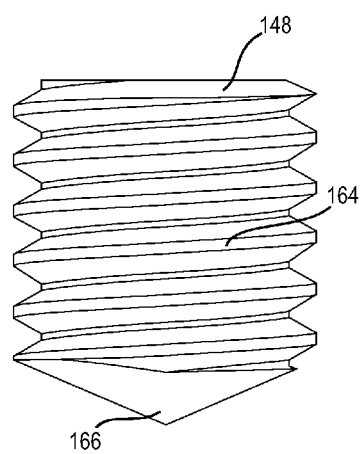
FIG. 25 is a side view of a screw usable with a spinal implant according to an exemplary embodiment.
Figure 26:
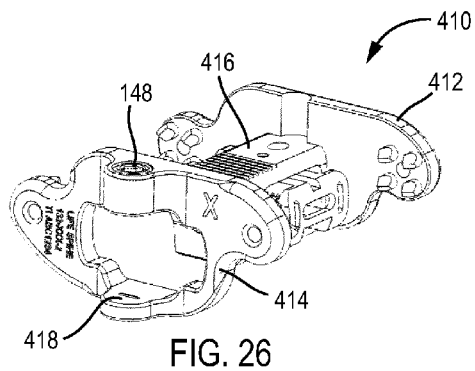
FIG. 26 is a perspective view of a spinal implant according to another exemplary embodiment.

According to one embodiment, projection 116 is an elongated member having a bull-nosed end 154 opposite first arm 112. Projection 116 includes a posterior surface 158 having a plurality of notches 152. A screw 148 such as a set screw extending through second arm 114 may be configured to engage one of notches 152 after second arm 114 is adjusted to a desired position relative to first arm 112. In some embodiments, additional notches may be provided on other surfaces of projection 116 (e.g., the anterior surface, etc.). As shown in FIG. 25, in one embodiment, screw 148 is a set screw having a threaded, cylindrical body portion 164 and a generally conical tip 166 extending from body portion 166. Tip 166 engages one of notches 152 to securely fasten second arm 114 relative to first arm 112.

Furthermore, the superior and inferior surfaces of projection 116 may include expanding portions 156 that are configured to expand superiorly/inferiorly relative to projection 116 to engage adjacent vertebral bodies. In some embodiments, expanding portions 156 include a textured surface configured to enhance the gripping action between projection 116 and the adjacent vertebral bodies. The adjustment of expanding portions 156 may be controlled via an adjustment screw 132 (e.g., through a worm gear, rack and pinion mechanism, etc.) such that the expanding portions may be adjusted after insertion of implant 110.

According to an exemplary embodiment, first arm 112, second arm 114, and/or projection 116 may include one or more recesses, apertures, etc. intended to receive bone growth or other similar materials. Furthermore, one or both of first arm 112 and second arm 114 may includes one or more bone screw bores 160 configured to enable insertion of a bone screw through implant 110 and into the bone structure of a vertebral body.

Referring now to FIGS. 21-23, an implant 210 is shown according to an exemplary embodiment. Implant 210 may share many features with implant 110. For example, implant 210 includes a first arm 212, a second arm 214, and a projection 216 that enables adjustment of second arm 214 relative to first arm 212. First arm 212 includes an upper portion 218, a lower portion 220, and a middle portion 222. Second arm 214 includes an upper portion 234, a lower portion 236, and a middle portion 238. Spikes 224, 226 extend from the inward facing surfaces of first and second arms 212, 214, respectively. Projection 216 extends from first arm 212 through a bore 250 in second arm 214.

According to an exemplary embodiment, projection 216 includes first and second extensions 260, 262 (e.g., members, projections, etc.). Extensions 260, 262 are generally elongated members and are parallel to one another to define a slot 241. As shown in FIGS. 22-23, extensions 260, 262 are separated by a generally straight connecting portion 242 that extends from upper portion 234 to lower portion 236 of second arm 214 and is defined by middle portion 238. In one embodiment, first extension 260 is received within bore 250 in second arm 214 and connecting portion 242 is received in slot 241. Bore 250 may be D-shaped, and one or more sides of first extension 260 may generally conform to the D-shape of bore 250. The D-shaped bore is defined by a linear base or front side, a pair of spaced apart linear outer second and third sides extending from the first side, and a curved side extending between the second and third sides. According to other embodiments, bore 250 may take other shapes to provide other functionality or engagement performance.

In one embodiment, first extension 260 is received within bore 250 and second extension 262 is disposed outside of bore 250 and connecting portion 242 as second arm 214 is adjusted relative to first arm 212. First extension 260 includes a U-shaped channel 264 (i.e., having a generally linear base and side edges and a curved side) that extends along all or a portion of first extension 260. One or both of first extension 260 and second extension 262 may include additional recesses, apertures, etc. such as aperture 266 shown in FIG. 23 for receiving bone growth or other materials.

As shown in FIGS. 21-23. projections 260, 262 may be configured to have a relatively close fit within and around bore 250 and connecting member 242, such that the orientation of second arm 214 is maintained and undesirable rotation, etc. of second arm 214 is prevented. Utilizing a connecting member 242 that separates extensions 260, 262 and provides an orientation guide may provide improved guidance for second arm 214 relative to other designs.

In one embodiment, projection 216 is slidably received within a channel 226 formed in first arm 212 such that projection 216 may be adjusted in an anterior/posterior fashion relative to first arm 212. Once positioned in a desired location, projection 216 may be secured using a threaded fastener, friction fit, etc. The geometries of projection 216 and channel 226 may be configured so as to prevent separation of the components except, for example, by sliding projection 216 out of channel 226.

Figure 24:
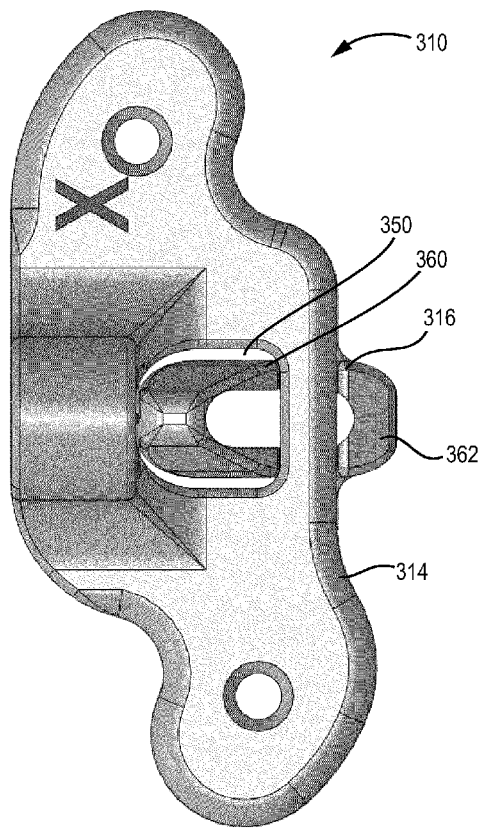
FIG. 24 is a side view of a spinal implant according to another exemplary embodiment.

Referring now to FIG. 24, a portion of an implant 310 similar to implant 210 is shown according to an exemplary embodiment. Implant 310 includes a second arm 314 having a generally D-shaped aperture 350 that receives a first extension 360 of projection 316. Projection 316 further includes a second projection 362. As shown in FIGS. 21-24, first projection 360 may be narrower in a superior/inferior direction than first extension 260, and may be wider in an anterior/posterior direction than first extension 260. Other configurations of first extensions 260, 360 and second extensions 262, 362 are possible according to various alternative embodiment.

Referring to FIGS. 26-30, an implant 410 is shown according to an exemplary embodiment, Implant 410 may share many features with the other implants disclosed herein, and includes a first arm 412, a second arm 414, and a projection extending between first and second arms 412, 414.

Figure 28:
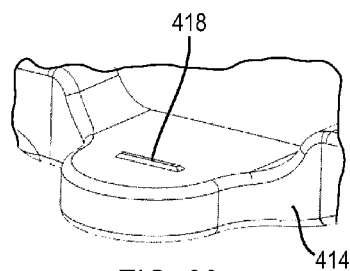
FIG. 28 is a partial perspective view of a portion of the spinal implant of FIG. 26 according to an exemplary embodiment.
Figure 27:
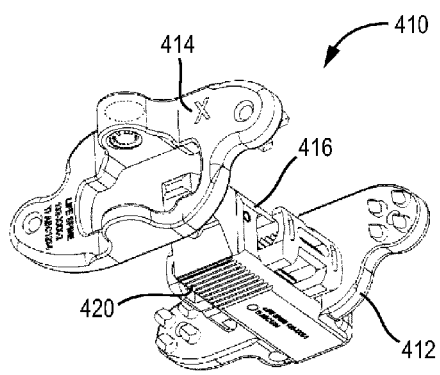
FIG. 27 is another perspective view of the spinal implant of FIG. 26 according to an exemplary embodiment.
Figure 29:
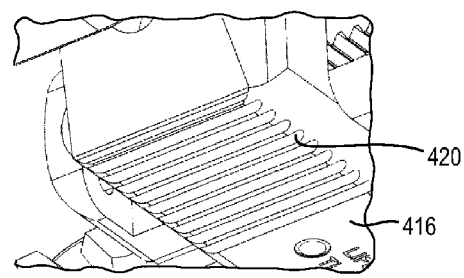
FIG. 29 is another partial perspective view of the spinal implant of FIG. 26 according to an exemplary embodiment.
Figure 30:
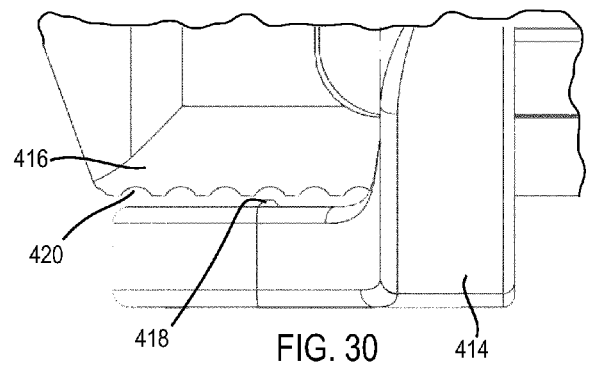
FIG. 30 is a partial side view of the spinal implant of FIG. 26 according to an exemplary embodiment.

As shown in FIGS. 28-29, according to an exemplary embodiment, second arm 414 includes a projection 418 (e.g., a tang, an elongated raised portion, etc.) and projection 416 includes a series of notches, or grooves, 402. As shown in FIG. 30, projection 418 and grooves 420 are positioned such that projection 418 fits at least partially within one of grooves 420 when first arm 412 is in a desired position relative to second arm 414. Grooves 420 may be any desired size, and may be spaced at any desired intervals (e.g., regular intervals, irregular intervals, etc.).

A set screw such as set screw 148 may be tightened so as to push projection 418 into one of grooves 420. In some embodiments, implant 410 may be configured such that prior to tightening set screw 148, projection 418 is able to move freely and spaced apart from grooves 420, and only upon tightening of screw 148 does projection 418 come to reside within one of the grooves. In other embodiments, implant 410 may be configured such that prior to tightening screw 148, projection 418 tends to contact grooves 420 as first arm 412 is moved relative to second arm 414, thereby providing a ratcheting or similar feel during adjustment of implant 410.

While FIGS. 26-30 show a single projection 418 engagable with a plurality of grooves 420, according to various other embodiments, more projections may be utilized, and the size, position, and spacing of the projection(s) and/or grooves may be varies to provide a desirable adjustability of implant 410. Furthermore, the projection/grooves may be utilized in combination with any of the other embodiments disclosed elsewhere herein. Further yet, the relative positions of the projection/grooves may be reversed in some embodiments.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal implant comprising:
   a first arm having a first upper portion and a first lower portion extending from a first middle portion, the first upper portion, the first lower portion, and the first middle portion defining a generally planar first inward facing surface, the first inward facing surface intersecting a first lateral side to define a first peripheral edge;
   a projection extending from the first middle portion of the first arm;
   a second arm having a second upper portion and a second lower portion extending from a second middle portion, the second middle portion defining a bore configured to slidably receive the projection to enable adjustment of the second arm relative to the first arm, the second upper portion, the second lower portion, and the second middle portion defining a generally planar second inward facing surface, the second inward facing surface intersecting a second lateral side to define a second peripheral edge;
   at least one spike integrally extending in a generally perpendicular fashion from each of the first and second inward facing surfaces;
   a first pointed member integrally extending from the first peripheral edge in a non-perpendicular fashion relative to the first inward facing surface; and
   a second pointed member integrally extending from the second peripheral edge in a non-perpendicular fashion relative to the second inward facing surface;
   wherein the first and second inward facing surfaces are non-perpendicular to a longitudinal axis extending along the projection between the first and second arms; and
   wherein the first and second pointed members extend in an at least partially anterior direction to form an obtuse angle with the respective one of the first and second inward facing surfaces.

2. The spinal implant of claim 1, wherein the first pointed member and the second pointed member each comprise a cylindrical body portion and a pointed tip extending from the cylindrical body portion.

3. The spinal implant of claim 1, wherein the at least one spike comprises a plurality of spikes spaced apart from the first and second peripheral edges.

4. The spinal implant of claim 1, wherein the first and second inward facing surfaces define an acute angle therebetween.

5. A spinal implant comprising:
   a first arm comprising a first upper portion and a first lower portion extending from a first middle portion, the first upper portion, the first lower portion, and the first middle portion defining a generally planar first inward facing surface, the first inward facing surface intersecting a first lateral side at a first peripheral edge;
   a projection extending from the first middle portion of the first arm;
   a second arm comprising a second upper portion and a second lower portion extending from a second middle portion, the second middle portion defining a bore configured to slidably receive the projection to enable adjustment of the second arm relative to the first arm, the second upper portion, the second lower portion, and the second middle portion defining a generally planar second inward facing surface, the second inward facing surface intersecting a second lateral side at a second peripheral edge;
   a plurality of first spikes integrally extending in a generally perpendicular fashion from the first and second inward facing surfaces; and
   at least one second spike integrally extending in a non-perpendicular fashion from each of the first and second peripheral edges;
   wherein the projection defines a longitudinal axis extending from the first arm to the second arm, and wherein the first and second inward facing surfaces are each non-perpendicular relative to the longitudinal axis, and wherein the first and second inward facing surfaces define an acute angle therebetween; and
   wherein the at least one second spike extends in an at least partially anterior direction to form an obtuse angle with the respective one of the first and second inward facing surfaces.

6. The spinal implant of claim 5, wherein the at least one second spike extends from the first lower portion of the first arm and the second lower portion of the second arm.

7. The spinal implant of claim 5, wherein the projection comprises a posterior facing surface comprising a plurality of notches, and wherein each of the first and second inward facing surfaces defines an acute angle relative to the posterior facing surface of the projection.

8. The spinal implant of claim 7, further comprising a threaded screw disposed within the second middle portion of the second arm, the threaded screw comprising a conical tip configured to selectively engage one of the plurality of notches on the posterior facing surface of the projection based on a position of the second arm relative to the first arm.

9. The spinal implant of claim 5, wherein the projection comprises a body portion and superior and inferior textured surfaces configured to engage adjacent vertebral bodies, the superior and inferior textured surfaces being expandable relative to one another and the body portion.

* * * * *